United States Patent [19]

Gwon et al.

[11] Patent Number: 5,627,162

[45] Date of Patent: May 6, 1997

[54] METHODS AND MEANS FOR CONTROL OF PROLIFERATION OF REMNANT CELLS FOLLOWING SURGERY

[76] Inventors: Arlene E. Gwon, 8 Trafalgar, Newport Beach, Calif. 92660; Charles J. Hagemeier, 22261 Caminito Escobedo, Laguna Hills, Calif. 92653

[21] Appl. No.: 374,360

[22] Filed: Jan. 18, 1995

Related U.S. Application Data

[63] Continuation of Ser. No. 463,390, Jan. 11, 1990, abandoned.

[51] Int. Cl.$^6$ .................................................. A61K 31/70
[52] U.S. Cl. ........................................... 514/54; 536/55.1
[58] Field of Search .............................. 514/54; 536/55.1

[56] References Cited

U.S. PATENT DOCUMENTS

| | | | |
|---|---|---|---|
| 4,039,662 | 8/1977 | Hecht et al. | 514/59 |
| 4,328,803 | 5/1982 | Pape | 604/28 |
| 4,432,751 | 2/1984 | Emery et al. | 514/557 |
| 4,486,416 | 12/1984 | Soll et al. | 514/54 |
| 4,657,930 | 4/1987 | Emery et al. | 514/557 |
| 4,665,089 | 5/1987 | Siezen et al. | 514/422 |
| 4,716,224 | 12/1987 | Sakurai et al. | 536/55.1 |
| 4,778,815 | 10/1988 | Cash et al. | 514/359 |
| 4,778,828 | 10/1988 | Palmai et al. | 514/724 |
| 4,797,422 | 1/1989 | Testa et al. | 514/646 |
| 4,826,872 | 5/1989 | Terao et al. | 514/474 |
| 4,871,350 | 10/1989 | Lam et al. | 604/49 |
| 4,886,786 | 12/1989 | Lindstrom et al. | 514/54 |
| 4,965,253 | 10/1990 | Goldberg et al. | 514/54 |

FOREIGN PATENT DOCUMENTS

| | | |
|---|---|---|
| 1178206 | 11/1984 | Canada . |
| 0136782 | 4/1985 | European Pat. Off. . |
| 2110532 | 2/1982 | United Kingdom . |

OTHER PUBLICATIONS

Wedrich, A., et al Ophthalmologica, vol. 205(3), 125–30.1992.
Wedrich, A., et al. J.Cataract Refract. Surg., vol. 18(5), 500–5. Sep. 1992.
Ruusuvaara, P., et al. Acta Ophthalmol. (Denmark) vol. 68(6), 721–7, Dec. 1990.
Glaser, D.B., et al. Arch. Opthalmol. (U.S.) vol. 104(12), 1819–1824, Dec. 1986.
Pape, L.G. J. Am. Intraocular Implant. Soc. vol. 6(4), 342–3. Oct. 1980.
Gibson, Chemical Abstracts, vol. 108(4), 1988, No. 26987a.
Kita, Chemical Abstracts, vol. 113(2), 1990, No. 12153s.
Cole et al., *International Surgery* 59, 242 (1968).
Nissen et al., *British J. Ophthal.* 65, 63 (1981).
Roberts et al., *Investigative Ophthlamology & Visual Science* 25, 746 (1984).
Stark et al., *Ophthlamology* 92, 209 (1985).
Shizohara, Chemical Abstracts, vol. 106(14), 1987, No. 107919r.
Ling et al, Chemical Abstracts, vol. 108(2), 1988, No. 11056x.

*Primary Examiner*—Elli Peselev

[57] ABSTRACT

The present invention relates to methods to control undesired cell proliferation of remnant cells following surgery, by applying an effective amount of at least one proteoglycan-type substrate adhesion molecule (SAM) to the site of surgery. SAMs, in particular chondroitin sulfate, hyaluronic acid, and non-toxic, pharmaceutically acceptable salts thereof, alone or in a composition form, are typically used to prevent or inhibit growth of lens-related cells in a lens capsule after surgical removal of the lens, or to prevent proliferative vitreoretinopathy following retinal reattachment procedure performed with or without vitrectomy.

10 Claims, 3 Drawing Sheets

1

METHODS AND MEANS FOR CONTROL OF PROLIFERATION OF REMNANT CELLS FOLLOWING SURGERY

This is a continuation of application Ser. No. 07/463,390, filed on Jan. 11, 1990, now abandoned.

FIELD OF THE INVENTION

The present invention concerns methods and means to control undesired proliferation of remnant cells following surgery. More particularly, the present invention relates to methods for prevention or inhibition of undesired cell proliferation by using substrate adhesion molecules (SAMs), in particular of the proteoglycan-type, such as chondroitin sulfate, hyaluronic acid, and non-toxic, pharmaceutically acceptable salts thereof, and to compositions containing such compounds, in combination with suitable delivery vehicles. SAMs, such as chondroitin sulfate, alone or in a composition form may, for example, be used to prevent or inhibit growth of lens-related cells in a lens capsule after surgical removal of the lens or to prevent proliferative vitreoretinopathy following retinal reattachment procedure performed with or without vitrectomy.

BACKGROUND ART

The percentage of population over the age of 65 increases in most developed countries, and so does the incidence of cataracts in this high risk age group. A cataract is a progressive clouding of the natural crystalline lens of the eye which obstructs the passage of light to the retina. Functional blindness can occur when the lens becomes substantially opaque.

As treatment for cataracts surgical removal of the lens from the lens capsule and insertion of an intraocular lens is commonly indicated. Only in the United States well over 1 million people have cataract surgery every year to remove a clouded natural lens, and over 95% of the patients involved have an intraocular lens implanted to allow them to clearly see again. As the retirement-age population increases., the incidence of such procedure is also expected to increase.

One of the most common complications of this surgical procedure is cellular proliferation in the capsular bag, with subsequent capsule wrinkling and opacification. "Secondary cataract" formation is a proliferation and transformation of cells on the lens capsule occurring in approximately 17–30% of patients receiving intraocular lenses within the year following surgery. In subsequent years, the percentage of patients experiencing such ingrowth increases. In recent studies, the incidence of secondary cataract formation has been reported to be 15–50% in adult patients with a 2 to 7 year follow up, and nearly 100% in the pediatric age group. [See, for example, Maltzman et al., *Ophthalmic Surgery* 20(5), 321–324 (1989); Nishi, O., *J. Cataract Refractive Surgery* 12, 510–552 (1986); Henahan, S., *Ophthalmology Times* 13(1), 10, 12 Dec. 15 (1988).]

While the causative factors involved in secondary cataract formation are unknown, the process is characterized by:

1. lens epithelial cell migration, proliferation and myoblastic transformation;

2. collagen production by these epithelial cells and fibrous membrane formation; and 3. wrinkling of the posterior capsule due to contraction of myoblastic cells [McDonnell et al., *Ophthalmology* 90, 1548–1553 (1983); McDonnel et al., *Ophthalmology* 91, 853–856 (1984)].

Complete removal or destruction of all lens epithelial cells in the lens capsule and control of inflammatory cells is imperative if such complications are to be avoided. During routine extracapsular cataract extraction, with or without lens insertion, every effort is made to completely remove all lens cells and control inflammation. However, these efforts, to date, have not been entirely successful primarily due to the fragmentation of the lens tissue during surgical removal and the difficulty of removing every lens-related cell.

Current therapy for the prevention of secondary cataract formation includes the use of postoperative steroids and refinements in surgical techniques (such as Aniz technique) to decrease breakdown of the blood aqueous barrier. The preferred method is Neodymium YAG Laser Capsulotomy which is not without complications. The main intraoperative complication of this technique is damage to the intraocular lens optic, occurring in about 20% of cases in a large survey [Stark et al., *Opthalmology* 92, 209–212 (1985)]. While usually clinically insignificant, a dense pattern of so called "lens dings" can affect visual acuity. Other operative complications include rupture of the anterior hyaloid and vitreous prolapse, corneal edema, iris bleeding and damage, transient elevation of intraocular pressure, cystoid macular edema, retinal detachment and pupillary-block glaucoma.

In search of methods associated with extracapsular cataract surgery which would prevent or delay the onset of secondary cataract formation, various approaches are known in the art. Modifications in the design of intraocular lenses (IOLs) have been reported to bring certain results. For example, contact between the optic of an IOL and the posterior capsule has been described to maintain the clarity of the central capsule.

Other attempts to avoid or delay secondary cataract formation focus on cellular kill, using cytotoxic agents, such as antiproliferatives (methotrexate, retinoic acid); immunotoxins (human lens epithelial surface antibody conjugated to Ricin A, basement membrane collagen conjugated to methotrexate); chemical debridement (EDTA and trypsin); mechanical debridement (ultrasound, cryotherapy).

Roy et al., *Medical Journal* 175–178 (1979) describe animal studies concerning the use of vincristine and vinblastine to inhibit subcapsular epithelial cell growth. Although they had a direct inhibitory effect on cell mitosis, these highly toxic chemicals were found to inhibit corneal wound healing and had deleterious side-effects on the cornea and iris. Radiation applied the second day after surgery was reported to be more effective, but the risk of radiation therapy in human eye is prohibitive as to its application.

According to the Canadian Patent No. 1,178,206 proliferation of remnant lens epithelial cells is prevented by an effective dose of the mitotic inhibitor methotrexate or retinoic acid or a combination of the two inhibitors. Osmotically balanced solutions of the same compounds for preventing posterior lens capsule opacification are disclosed in the U.S. patent Specification No. 4,657,930.

A different approach to the inhibition of remnant lens epithelial cells after extracapsular extraction is the use of monoclonal antibodies specific to residual lens epithelial cells which can be used to destroy these cells selectively, without damage to other parts of the eye at the time of the cataract removal (see U.S. Pat. No. 4,432,751).

Immunotoxins comprising antibodies specific to the proliferative cells conjugated to an antiproliferative agent, are disclosed in the U.S. patent application Ser. No. 168,697, filed Mar. 16, 1988, assigned to Allergan, Inc.

Although some of the prior art methods have promising results, they either employ highly toxic chemicals or dangerous radiation treatments, or use antibodies and antibody-conjugates, which have to be produced in a lengthy and rather expensive procedure. Accordingly, there is a great need for an effective and simple procedure for ensuring the complete removal and/or destruction of lens cells and other proliferative cells from the lens capsule prior to implantation of the intraocular lens.

In addition to the removal of natural lens due to cataract formation, there are additional ocular surgical procedures where proliferation of remnant cells is to be avoided. Such procedures include retinal reattachment procedures and vitrectomy, that are being performed at ever increasing rates.

Surgical replacement of the vitreous, and scleral buckling procedures are commonly indicated as treatment for retinal tears, traction retinal detachment and opacities in the vitreous from various causes including but not limited to, diabetic retinopathy, proliferative vitreoretinopathy, vitreous hemorrhage, endophthalmitis, etc. In these procedures, retinal pigment epithelial cells, fibroblasts and glial cells create contractile cellular membranes and thereby cause traction retinal detachment.

Proliferative vitreoretinopathy is the major cause of failure after retinal reattachment surgery and vitrectomy. This disorder is characterized by the formation of cellular membranes within the vitreous cavity which cause traction retinal detachments.

Proliferative vitreoretinopathy generally results from migration of the retinal pigment epithelial cells, fibroblasts and glial cells into the vitreous cavity. Any cellular proliferation in the vitreous is to be avoided if proliferative vitreoretinopathy is to be prevented. To illustrate the seriousness of this problem, in a series of 1088 eyes, proliferative vitreoretinopathy was the most common cause of failure (27%) following retinal detachment surgery.

Accordingly, there is a great need for an effective and simple procedure for avoiding cellular proliferation following retinal reattachment procedures (with or without vitrectomy). The approaches employed so far for complete removal and/or destruction of migrating retinal pigment epithelial cells, were not entirely successful. Similar problems are encountered in other, non-ocular surgical procedures. For example, the long-term success of the surgical removal of certain tumors, e.g. breast tumors, is greatly dependent on how efficiently all tumor-related cells can be removed and/or destroyed. Not sufficient control of tumor cell proliferation may result in the reoccurrence of tumor.

Therefore, there is a great need for a method that could reliably prevent or, at least, limit regrowth of cells following such surgeries.

SUMMARY OF THE INVENTION

The present invention relates to methods to control unwanted cell proliferation by means of substrate adhesion molecules (SAMs), in particular proteoglycans, such as chondroitin sulfate, hyaluronic acid, and non-toxic, pharmaceutically acceptable salts thereof, and to compositions comprising such compounds in association with suitable delivery vehicles. When instilled into a body cavity following surgery, SAMs, e.g. chondroitin sulfate alone or in composition form, eliminate or inhibit unwanted cell proliferation.

In laboratory experiments we have instilled suitably viscous solutions of chondroitin sulfate into the peripheral lens capsular bag after lens removal, and have surprisingly found that in the eyes that received chondroitin sulfate there was no or little cell growth present in the capsular bag, and the capsule maintained its transparency for an extended period of time.

The present invention is based on the discovery that chondroitin sulfate and other substrate adhesion molecules, in particular from the group of proteoglycans, when instilled into a body cavity following a surgical procedure, effectively prevent regrowth of the residual cells. This is a novel approach for the elimination of the proliferation of remnant cells after surgical removal of a tissue, and in particular, for the prevention of secondary cataract formation. Whereas most prior investigators have focused on cellular kill, the data presented in this patent application suggest that interference in the regulatory processes of cellular adhesion and differentiation offers an alternative approach to the prevention of secondary cataract. Following cataract extraction, the contact inhibition provided by lens cortical fibers is lost and cells in the equatorial region are free to migrate, attach and proliferate along the posterior capsule. Although the role of substrate adhesion molecules in regulatory control of cell growth is not entirely understood yet, by interfering with these regulatory processes it appears to be possible to affect the myoblastic transformation of lens epithelial cells without damage to other intraocular structures.

In one aspect, the present invention relates to a method for control of proliferation of remnant cells of a body tissue following surgical removal of the tissue, by applying an effective amount of at least one proteoglycan-type substrate adhesion molecule to the site of surgery.

In another aspect, the invention relates to a method for control of the proliferation of remnant lens epithelial cells in the lens capsular bag following removal of the natural lens, by instilling an effective amount of at least one proteoglycan-type substrate adhesion molecule into the lens capsular bag.

In a further aspect, the present invention relates to a method for preventing proliferative vitreoretinopathy following retinal reattachment procedure with or without vitrectomy, by control of the proliferation of retinal pigment epithelial cells, comprising instilling an effective amount of at least one proteoglycan-type substrate adhesion molecule into the vitreous cavity over a retinal tear.

In a still further aspect, the invention relates to a method for control of the proliferation of remnant tumor cells following excision of a tumor, comprising instilling an effective amount of at least one proteoglycan-type substrate adhesion molecule into a body cavity from which the tumor has been excised.

In these methods the proteoglycan-type substrate adhesion molecule is preferably selected from the group of chondroitin sulfate, hyaluronic acid, and non-toxic, pharmaceutically acceptable salts of these compounds. These and similar substrate adhesion molecules may be applied alone or in combination with suitable delivery vehicles and/or with further substrate adhesion molecules of different type, such as fibronectin.

In a different aspect, the present invention relates to compositions for control of proliferation of remnant cells of a tissue following surgical removal of the tissue, comprising an effective amount of at least one proteoglycan-type substrate adhesion molecule, and at least one delivery vehicle providing sufficient retention time for chondroitin sulfate at the site of application to exert its activity.

If desired, the substrate adhesion molecule, such as chondroitin sulfate or a salt thereof, may be used in combination with other direct-acting antiproliferative agents known in the art or with agents that become cytotoxic upon subjection to an outside influence, or that participate in the generation of a separate cytotoxic moiety upon subjection to an outside influende (i.e. require "activation").

DETAILED DESCRIPTION OF THE INVENTION

1. Definitions and General Methods

Figure 1:
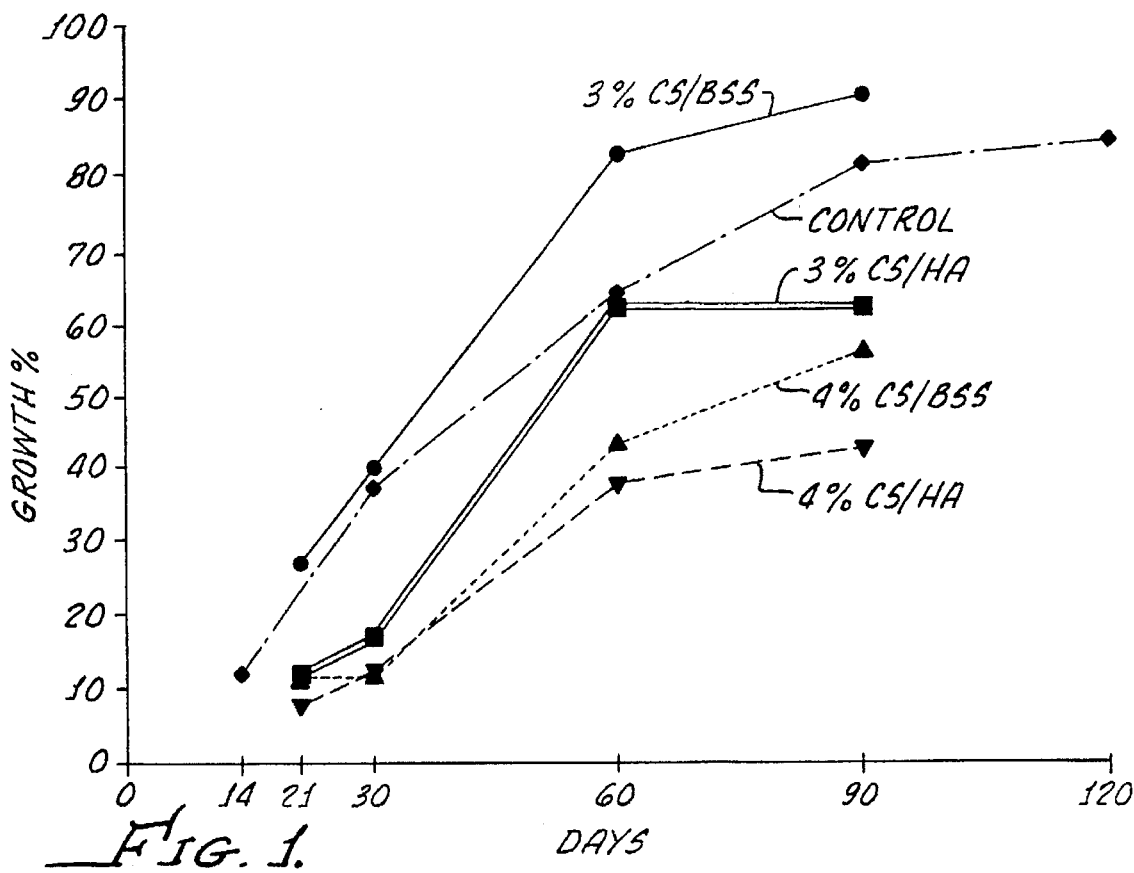
FIGS. 1 through 3 illustrate the effect of solutions containing various concentrations of chondroitin sulfate on the growth of epithelial lens cells in the eyes of rabbits, following removal of the natural lens.

Substrate adhesion molecules (SAMs) are usually found as components of the extracellular matrix (ECM), although some of them can bind to cells by means of particular receptors. They constitute one of the three main families of molecules that are involved in the adhesion of cells to each other and to substrates such as the ECM (the other two families being cell adhesion molecules, and cell junctional molecules). ECM is a very complex structure. In general, the major components making up ECM are various forms of collagens, various glycoproteins having different binding sites and structures (e.g., laminin, fibronectin, and cytotactin), and proteoglycans of various types. At the present, it is not clear in the art whether every ECM protein has a specific cell-associated receptor, or shows cell-binding capabilities. However, SAMs clearly include glycoproteins, such as laminin, fibronectin, and proteoglycans, such as chondroitin/dermatan sulfate. As to a more detailed definition, we refer to Gerald M. Edelman, "Topobiology", "An introduction to Molecular Embryology", Basic Books, Inc., Publ., New York, 1988, pp. 101–115.

Proteoglycans (also referred to as mucopolysaccharides, or glucosaminoglycans) constitute a group of structurally closely related SAMs found singly in some tissues, and as mixtures in others. A typical representative of these compounds is chondroitin sulfate.

Chondroitin sulfate (chondroitinsulfuric acid) is a generic term for high viscosity mucopolysaccharides (glycosaminoglycans) with N-acetylchondrosine as a repeating unit, and with one sulfate group per disaccharide unit, either in the 4- or in the 6-position. Their estimated molecular weight is approximately 50,000 depending on source and method of preparation. Chondroitin 4-sulfate and chondroitin 6-sulfate are the most abundant mucoglycosaccharides in the body, and occur both in skeletal and soft connective tissue. Chondroitin sulfates are known to have antihyperlipoproteinemic properties.

Another proteoglycan-type SAM is dermatan sulfate. Dermatan sulfate, an epimer of chondroitin 4-sulfate, contains L-iduronic acid in place of glucuronic acid at carbon atom 5, and is present in soft connective tissue and is abundant in skin, arterial walls and heart valves.

A further representative of the proteoglycan-type SAMs is keratan sulfate which is characterized by much more molecular heterogeneity than is the case with the chondroitin sulfates. The polysaccharide of keratans is principally composed of a repeating disaccharide unit consisting of N-acetylglucosamine and galactose. There are no uronic acids in the molecule. The total sulfate content varies, but there is ester sulfate present at carbon 6 of both the N-acetylglucosamine and the galactose residues. The so called keratan sulfate I occurs in the cornea, whereas keratan sulfate II occurs in skeletal tissues.

A further compound that is usually associated with proteoglycans, and is classified as proteoglycan for the purposes of the present invention, is hyaluronic acid. The repeating disaccharide units of this mucopolysaccharide consist of glucuronic acid linked to N-acetylglucosamine. Its composition is therefore similar to that of chondroitin, the essential difference being the occurrence of galactosamine in chondroitin instead of glucosamine in hyaluronic acid.

The mentioned proteoglycans and related compounds are well known in the art, and are, for example, described by Harper et al., in "Review of Physiological Chemistry" 17th Edition, Lange Medical Publications, Los Altos, Calif., 1977, pp. 457 to 663.

The term "substrate adhesion molecules of different type", as used in the claims and throughout the specification, refers to non-proteoglycan SAMs, preferably to glycoproteins, such as fibronectin, laminin, enactin, chondronectin, cytotactin, etc.

The methods of the present invention are usually performed with compositions containing substrate adhesion molecules in combination with suitable delivery vehicles. The main role of such delivery vehicles is to provide sufficient retention time for the substrate adhesion molecules at the site of application, to exert their activity. The compositions usually contain one or more SAMs in an aqueous medium, in combination with one or more delivery vehicles and/or further excipients conventionally used in pharmaceutical preparations for topical use. Some of the substrate adhesion molecules, such as hyaluronic acid, fibronectin, may also serve as delivery vehicles. Further preferred delivery vehicles include, but are not limited to, hydroxypropyl methylcellulose, carboxymethyl cellulose, polyacrylic acid, gelatin, and combinations of these compounds.

As hereinabove mentioned, the SAMs may be used in combination with other direct-acting antiproliferative agents known in the art, or with agents that require activation.

Direct-acting agents include folate inhibitors, pyrimidine analogs, purine analogs, alkylating agents and antibiotics.

Preferred agents that require activation include enzymes, photoactivated compounds photosensitizing compounds, alpha-emitting and beta-emitting radionucleotides, etc. Such agents are known in the art, and are, for example, detailed in the co-pending patent application Ser. No. 168,697 (filed Mar. 16, 1988), assigned to Allergan, Inc.

The term "control of proliferation" and grammatical variations thereof, are used herein to refer to the elimination or inhibition of the proliferation of remnant cells. The extent of inhibition should be sufficient to avoid or significantly reduce the occurrence of the detrimental consequences of remnant cell proliferation, detailed hereinabove.

The removal of natural lens and the insertion of an intraocular lens may be performed by any surgical procedure known in the art, small incision surgery being preferred. In a particularly preferred method, natural lens is broken into small fragments by ultrasound waves, and the fragments can be removed through a hollow needle (phacoemulsification). Phacoemulsification requires only an about 3 mm incision, compared to incisions of up to about 12 mm for ordinary techniques, and is less traumatic to the eye.

Appropriate antibodies for utilization in the present invention may be produced using conventional poly- and/or monclonal antibody-generation procedures. Certain antibodies specific to surface proteins of proliferative cells in the lens capsule are known. See, for example, U.S. Pat. No. 4,432,751 the disclosure of which is hereby expressly incorporated by reference.

In general, appropriate antibodies may be prepared by immunizing a mammal with appropriate cell surface antigen from the target proliferative cells. Conventional techniques may then be used to either isolate polyclonal antibody from the animal, or to generate monoclonal antibody in accordance with the well-known hybridoma techniques pioneered by Koehler and Milstein, Nature 256, 495–497 (1975).

2. Preferred Embodiments

Chondroitin sulfate or a non-toxic, pharmaceutically acceptable salt thereof may be used to control cell proliferation in the lens capsule after removal of the natural lens.

Surgical removal of lens material in an animal model, or in human, may be accomplished using conventional extracapsular phacoemulsification and irrigation/aspiration techniques. An effective amount of chondroitin sulfate or a salt thereof is then administered intraocularly into the peripheral capsular bag. Chondroitin sulfate or a salt thereof may be applied alone, or in combination with a suitable delivery vehicle as a viscous solution. An intraocular lens may be placed in the capsular bag either before or after the administration of chondroitin sulfate.

Similarly, the reattachment of the retina and vitrectomy in an animal model, or in human, can be accomplished using conventional retinal reattachment procedures with vitreous replacement. Prior to the close of surgery, an effective amount of chondroitin sulfate or a non-toxic, pharmaceutically acceptable salt thereof, is injected on the retinal tear or may be used to replace aspirated vitreous. Again, chondroitin sulfate or a salt thereof, may be employed alone, or in combination with a suitable delivery vehicle, in the form of a viscous solution.

The preferred delivery vehicle is hyaluronic acid or a pharmaceutically acceptable salt thereof. In a particularly preferred embodiment, compositions comprising 3–5% (w/v) chondroitin sulfate and 3% (w/v) hyaluronic acid (Viscoat®) are employed.

Other suitable delivery vehicles include, but are not limited to, carboxymethyl cellulose (CMC), CMC/gelatine, or other SAMs, such as fibronectin.

The compositions of the present invention may include further additives, generally used in the preparation of pharmaceutical formulations for topical use.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives and stabilizers.

Preferred preservatives that may be used in the pharmaceutical compositions of the present invention include, but are not limited to, benzalkonium chloride, chlorobutanol, thimerosal, phenylmercuric acetate and phenylmercuric nitrate. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

Other topical formulations include lotions, gels, creams, ointments, suspensions, emulsions. A wide variety of dermatologically acceptable inert excipients well known in the art may be employed. Typical excipients include, but are not limited to water, ethyl alcohol, stearyl alcohol, and gel-producing substances.

The optimum dosage for any particular condition may be determined empirically; and this determination is well within the knowledge of a skilled physician. Typical doses are illustrated in the Examples.

Non-toxic, pharmaceutically acceptable salts of chondroitin sulfate typically are ammonium or metal salts. Metal salts of chondroitin sulfate are readily formed with aqueous metal hydroxides, carbonates, hydrocarbonates, etc. in a known manner, the alkali metal (e.g. sodium, potassium), and alkali earth metal (e.g. calcium, magnesium) salts being preferred. The obtained metal salts can be readily converted back into the corresponding carboxylic acids, e.g. by aqueous mineral acids.

3 EXAMPLES

Example 1

Figure 4:
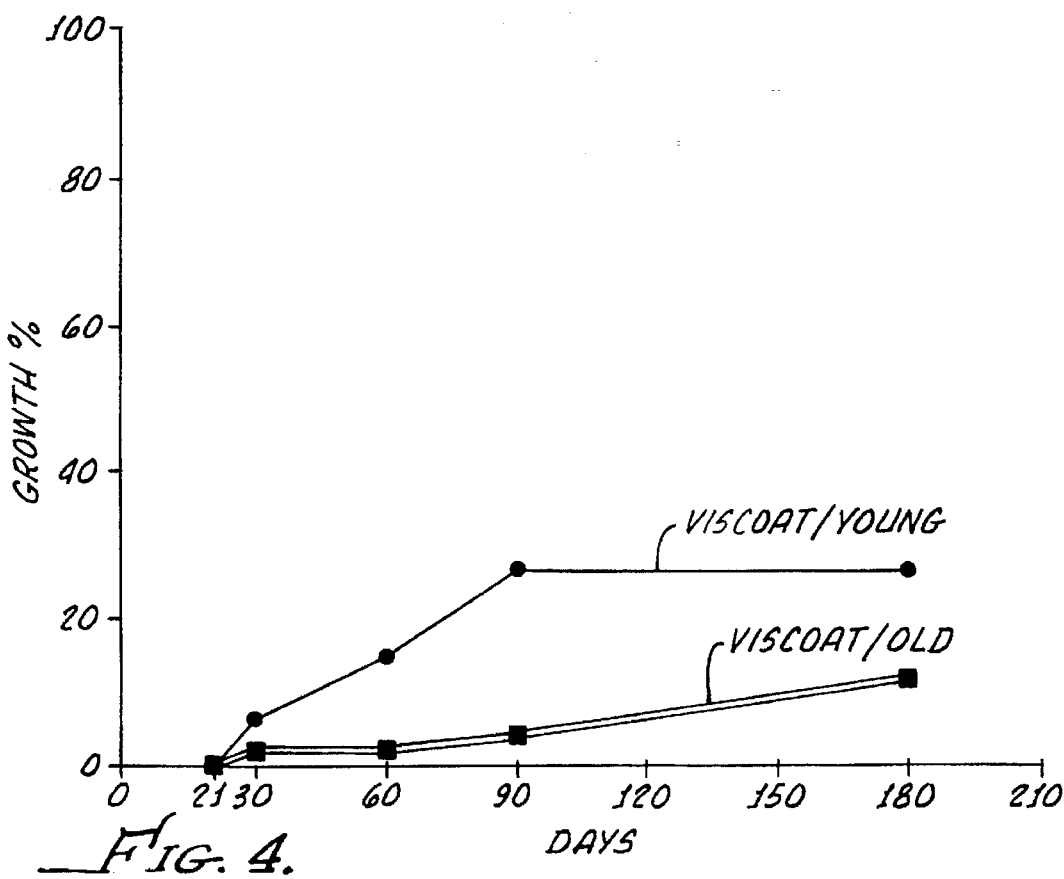
FIG. 4 shows the difference in lens epithelial cell regrowth upon Viscoat® treatment in the eyes of young and older rabbits.

The lenses of anesthetized rabbits (New Zealand Albino and Dutch Belt Crosses) were extracted through a small 3 mm anterior capsulotomy by endocapsular phacoemulsification and irrigation/aspiration technique. Following removal of the lens nucleus and cortex, the empty capsular bag was filled with 0.1 to 0.2 ml of hyaluronic acid (Healon®) or chondroitin sulfate/hyaluronic acid (Viscoat®). Both in the chondroitin sulfate-treated and in the control group young (3 months) and older (6 months) rabbits were treated separately. The Viscoat®-treated group contained 2 animals, and 3 animals were treated with Healon®. At 18 months, regenerated lens material fills the capsular bag in the eyes that received Healon®. In the eyes that received Viscoat® there is little or no growth present in the capsular bag and the capsule is fairly translucent upon retro illumination by slit lamp examination. The results are illustrated in FIG. 4.

Example 2

The lenses of anesthetized New Zealand Albino rabbits were extracted through a 3 mm anterior capsulotomy by endocapsular phacoemulsification and irrigation/aspiration techniques. Following removal of the lens nucleus and cortex, the empty lens capsular bag was filled with 0.2 to 0.4 ml of various concentrations of chondroitin sulfate in balanced salt solution, chondroitin sulfate in 1% sodium hyaluronate, 1% sodium hyaluronate or balanced salt solution. The number of rabbits in the various groups was between 5 and 9.

Figure 2:
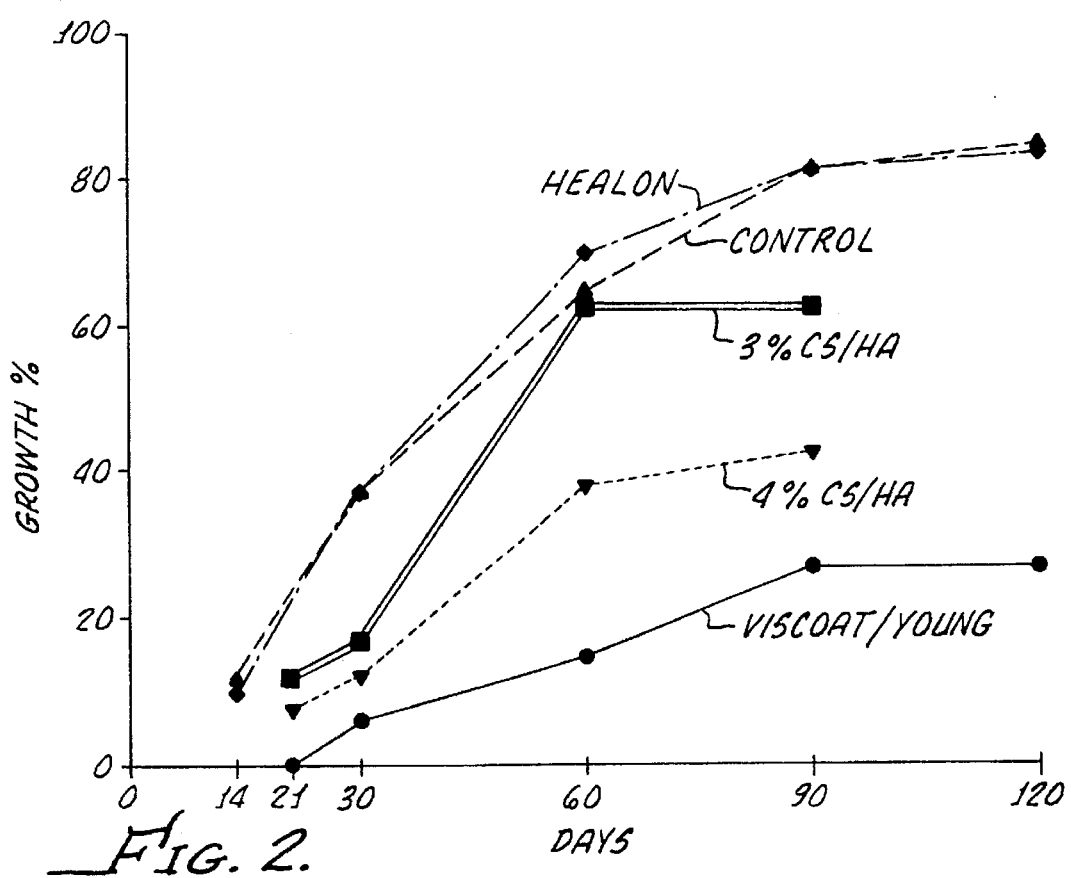
Figure 3:
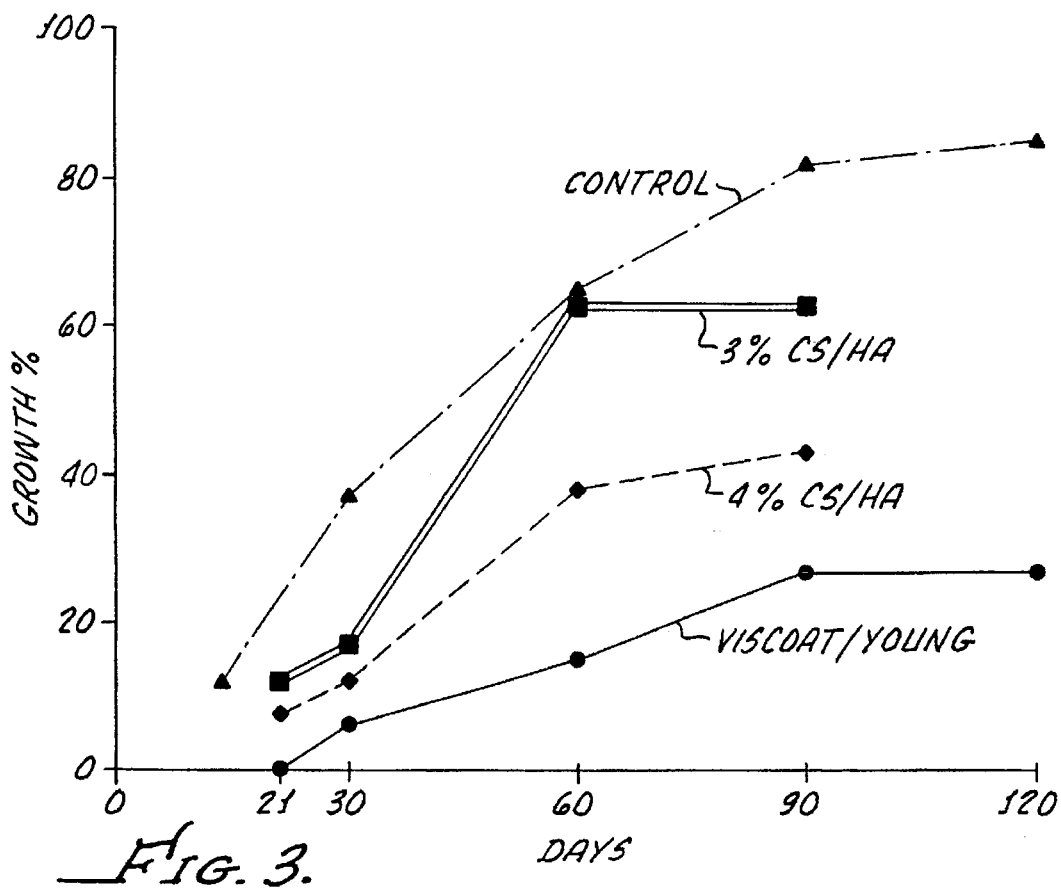

Rabbits receiving chondroitin sulfate had a dose related decrease in lens regrowth which was greater when combined with hyaluronic acid and most pronounced in Viscoat® (FIGS. 1, 2 and 3).

The rabbits receiving 5% chondroitin sulfate in hyaluronic acid had less than 10% growth at one and 2 months after application.

These studies indicate that chondroitin sulfate has an inhibitory effect on lens regeneration following endocapsular lens extraction in rabbits, which is accentuated when chondroitin sulfate is formulated with hyaluronic acid and which is better than the effect of balanced salt solution (BSS) alone or hyaluronic acid alone.

Example 3

The lenses of anesthetized New Zealand albino rabbits were extracted following removal of the anterior lens capsule by extracapsular phacoemulsification and irrigation/aspiration techniques. Following removal of the lens nucleus and cortex, the peripheral lens capsular bag (where the remnant of the anterior capsule remained behind the iris) was filled with hyaluronic acid, 4% chondroitin sulfate (CS)/1% hyaluronic acid (HA), or Viscoat®. Animals in the untreated control group received no injection. The number of rabbits in the various groups was between 1 and 3.

Rabbits which received 4% CS/1% HA or Viscoat® had fairly clear posterior capsules 6 months after operation/treatment.

Example 4

Second passage rabbit lens epithelial cells were seeded into 6-well culture dishes at a density of 42,000 cells per well. After 24 hours, a Day 0 baseline cell count was taken, and chondroitin sulfate (CS) at final concentrations of 0, 0.1, 0.5, 1.0, 5.0 and 10.0% (w/v) was added. Three culture wells were counted for every data point, using the Coulter counter. Cell counts were determined every 24 hours for 6 days. On day 6, only the cell counts for the controls and for CS at 5% and 10% were available, due to the limited supply of CS.

Figure 5:
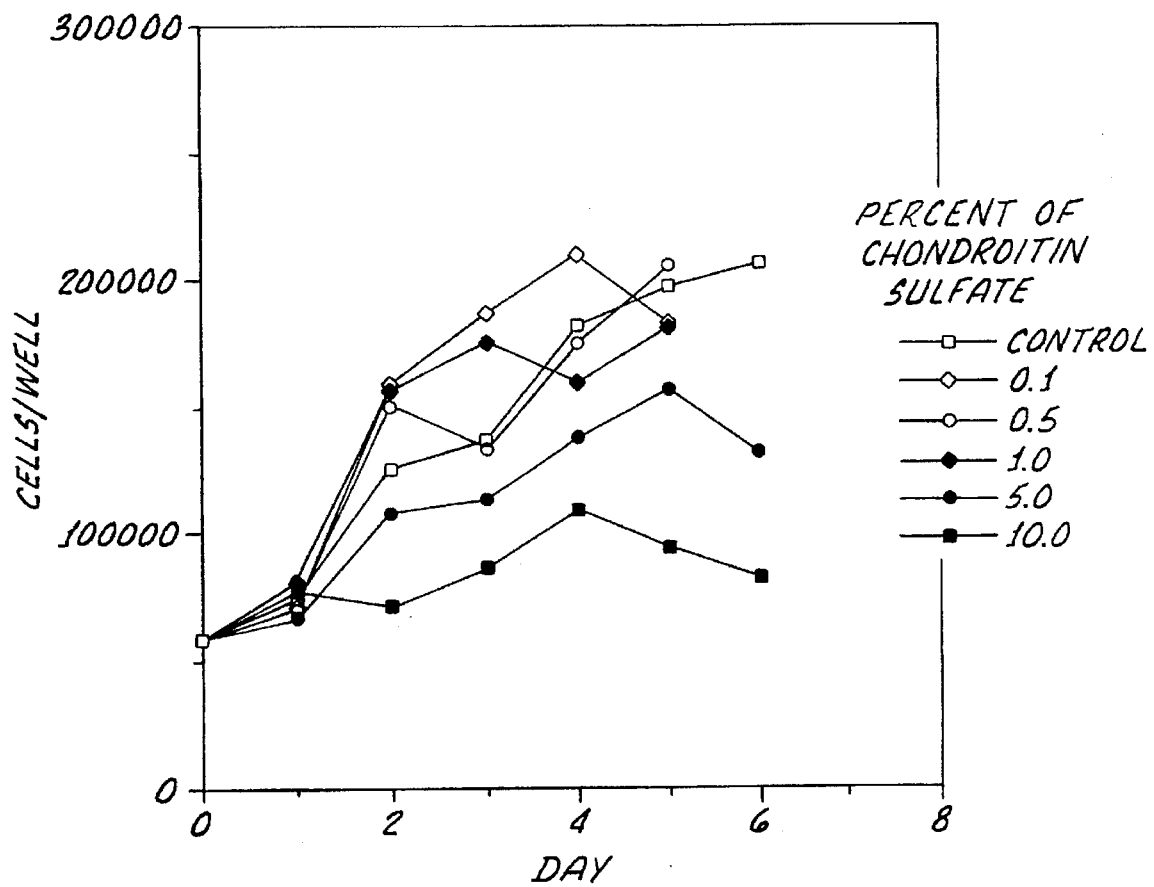
FIG. 5 illustrates the effect of various concentrations of chondroitin sulfate on rabbit lens epithelial cells in cell culture.

The results of this experiment are represented graphically in FIG. 5. Each point of the graph is an average of three data points. After day 1, CS at the two highest concentrations (5% and 10%) inhibited cell growth in a dose-dependent manner. A slight increase in cell number was present at the lower concentrations between days 1 and 4, however, this increase did not prove to be consistent at day 5.

Chondroitin sulfate at concentrations of 5% or more significantly inhibited the growth of lens epithelial cells in culture. Increases in cell number, due to lower concentrations of chondroitin sulfate, were small and insignificant.

The foregoing description details specific methods and compositions that can be employed to practice the present invention. In view of this specific teaching, the art skilled will well enough know how to devise alternative reliable methods and compositions for arriving at essentially the same results. Similarly, although the specific examples illustrate the ophthalmic use of the methods and compositions according to the present invention, this teaching can easily be extended to other medical areas, where the elimination of cell proliferation following surgery is required. Thus, however detailed the foregoing may appear in text, it should not be construed as limiting the overall scope hereof; rather, the ambit of the present invention is to be governed only by the lawful construction of the appended claims.

We claim:

1. A method for control of the proliferation of remnant epithelial cells in a remaining lens capsular bag structure following removal of the natural lens, comprising applying an effective amount of a mixture of chondroitin sulfate and hyaluronic acid directly into the remaining lens capsular bag structure.

2. The method according to claim 1, wherein said mixture is applied directly into the lens capsular bag after placement of an intraocular lens into said capsular bag.

3. The method according to claim 1, wherein direct application of said mixture is followed by placement of an intraocular lens into said capsular bag.

4. The method according to claim 1, wherein said mixture is directly applied in combination with at least one delivery vehicle providing sufficient retention time at the site of application to exert its activity.

5. A method according to claim 4, wherein said delivery vehicle is selected from the group consisting of hydroxypropyl methylcellulose, carboxymethyl cellulose and polyacyrylic acid.

6. A method according to claim 5, wherein carboxymethyl cellulose is employed in combination with gelatin.

7. The method according to claim 1, wherein said mixture is applied in combination with fibronectin.

8. A method for the control of the proliferation of remnant epithelial cells in a remaining lens capsular bag structure following removal of the natural lens comprising applying a mixture of from 1 to 10 percent of chondroitin sulfate and 1 to 3 percent hyaluronic acid, w/v, into the remaining lens capsular bag structure.

9. The method of claim 8 wherein said mixture comprises from 3 to 5 percent chondroitin sulfate and 3 percent hyaluronic acid.

10. The method according to claim 8, wherein said mixture is applied directly into the lens capsular bag after placement of an intraocular lens into said capsular bag.

* * * * *

UNITED STATES PATENT AND TRADEMARK OFFICE
CERTIFICATE OF CORRECTION

PATENT NO. : 5,627,162
DATED : May 6, 1997
INVENTOR(S) : Gwon et al

It is certified that error appears in the above-identified patent and that said Letters Patent is hereby corrected as shown below:

On the title page, insert; --Attorney, Agent, or Firm--J. Mark Hoch; Robert J. Baran; Martin A. Voet Column 1, line 40; after "increase" delete "."

Column 4, line 67; delete "influende" and insert in place thereof --influence--

Signed and Sealed this

Twenty-first Day of October 1997

Attest:

BRUCE LEHMAN

Attesting Officer

Commissioner of Patents and Trademarks